United States Patent [19]

Polansky et al.

[11] Patent Number: 5,674,888
[45] Date of Patent: Oct. 7, 1997

[54] METHOD FOR THE TREATMENT OF A TRABECULAR MESHWORK WHOSE CELLS ARE SUBJECT TO INHIBITION OF CELL DIVISION

[75] Inventors: Jon R. Polansky, Mill Valley; Ernest Bloom, Alamo; Donald J. Fauss, San Francisco, all of Calif.

[73] Assignee: University of California, Alameda, Calif.

[21] Appl. No.: 486,255

[22] Filed: Jun. 7, 1995

[51] Int. Cl.$^6$ ............................................. A61K 31/40
[52] U.S. Cl. ...................... 514/418; 514/420; 514/912
[58] Field of Search .................................... 514/418, 420, 514/912

[56] References Cited

U.S. PATENT DOCUMENTS

| | | | |
|---|---|---|---|
| 2,798,053 | 7/1957 | Brown | 260/2.2 |
| 3,732,865 | 5/1973 | Higuchi et al. | 128/260 |
| 3,773,919 | 11/1973 | Boswell et al. | 424/19 |
| 3,887,699 | 6/1975 | Yolles | 424/19 |
| 4,136,250 | 1/1979 | Mueller et al. | 528/29 |
| 4,192,827 | 3/1980 | Mueller et al. | 525/123 |
| 4,327,725 | 5/1982 | Cortese et al. | 128/260 |
| 4,454,151 | 6/1984 | Waterbury | 424/274 |
| 4,522,826 | 6/1985 | Sunshine et al. | 514/569 |
| 4,543,251 | 9/1985 | Kamishita | 424/81 |
| 4,548,990 | 10/1985 | Mueller et al. | 525/123 |
| 4,617,299 | 10/1986 | Knepper | 514/178 |
| 4,670,254 | 6/1987 | Kamishita | 424/81 |
| 4,690,927 | 9/1987 | Voss et al. | 514/282 |
| 4,711,782 | 12/1987 | Okada et al. | 424/455 |
| 4,711,906 | 12/1987 | von Stetten et al. | 514/561 |
| 4,757,060 | 7/1988 | Lukacsko et al. | 514/160 |
| 4,757,089 | 7/1988 | Epstein | 514/571 |
| 4,777,174 | 10/1988 | Sunshine et al. | 514/264 |
| 4,829,088 | 5/1989 | Doulakas | 514/567 |
| 4,855,293 | 8/1989 | Collington et al. | 514/212 |
| 4,876,250 | 10/1989 | Clark | 514/179 |
| 4,880,742 | 11/1989 | Hayaishi et al. | 435/238 |
| 4,904,649 | 2/1990 | Schwartz | 514/174 |
| 4,917,886 | 4/1990 | Asche et al. | 424/81 |
| 4,948,805 | 8/1990 | Ziggiotti et al. | 514/428 |
| 4,960,799 | 10/1990 | Nagy | 514/567 |
| 4,971,802 | 11/1990 | Tarcsay et al. | 424/450 |
| 4,973,469 | 11/1990 | Mulligan et al. | 424/461 |
| 4,980,170 | 12/1990 | Schneider et al. | 424/451 |
| 4,999,379 | 3/1991 | Fankhauser | 514/567 |
| 5,036,097 | 7/1991 | Floyd et al. | 514/400 |
| 5,110,493 | 5/1992 | Cherng-Chyi et al. | 514/413 |
| 5,124,154 | 6/1992 | Babcock et al. | 424/427 |
| 5,190,762 | 3/1993 | Yarosh | 424/450 |
| 5,192,535 | 3/1993 | Davis et al. | 424/78.04 |
| 5,200,453 | 4/1993 | Janssen | 514/399 |
| 5,270,052 | 12/1993 | Gelfand et al. | 424/450 |
| 5,304,561 | 4/1994 | Faezeh . | |
| 5,314,909 | 5/1994 | Dollerup | 514/420 |
| 5,474,985 | 12/1995 | Polansky et al. | 514/26 |

FOREIGN PATENT DOCUMENTS

| | | |
|---|---|---|
| 1176565 | 10/1984 | Canada . |
| 0 058481 A1 | 8/1982 | European Pat. Off. . |
| 0 133988 A2 | 3/1985 | European Pat. Off. . |
| 0 158277 A2 | 10/1985 | European Pat. Off. . |
| 0 160408 A1 | 11/1985 | European Pat. Off. . |
| 0 306 984 | 3/1989 | European Pat. Off. . |
| 0 390071 A1 | 10/1990 | European Pat. Off. . |
| 0 422681 A1 | 4/1991 | European Pat. Off. . |
| 0 466650 A2 | 1/1992 | European Pat. Off. . |
| 0 550921 A1 | 7/1993 | European Pat. Off. . |
| 58-152811 | 9/1983 | Japan . |
| 62-123119 | 6/1987 | Japan . |
| WO 89/06964 | 8/1989 | WIPO . |
| WO 91/05771 | 5/1991 | WIPO . |
| WO 91/16896 | 11/1991 | WIPO . |
| WO 91/19482 | 12/1991 | WIPO . |
| WO 92/00044 | 1/1992 | WIPO . |
| WO A 95 09639 | 4/1995 | WIPO . |
| WO A9517178 | 6/1995 | WIPO . |

OTHER PUBLICATIONS

The Merck Index, Eleventh Edition, 1989. pp. 786 and 787.

Alvarado, J.A. et al.—*Human Trabecular Cells*, Invest. Ophthalmol. Vis. Sci. 23:464–478 (1982).

Babizhayev, M.A. et al.—*Lipid Peroxidation in Open–angle Glaucoma*, Invest. Opthalmol. Vis. Sci. 67:371–377 (1989).

Bengtsson, B.—*Incidence of Manifest Glaucoma*, British J. of Ophthalmology, 73:438–487 (1989).

Bhuyan, K.C. et al.—*Regulation of Hydrogen Peroxide in Eye Humors: Effect of 3–Amino–1H–1,2,4–Triazole on Catalase and Glutathione Peroxidase of Rabbit Eye*, Biochmica et Biophysica Acta 497:641–651 (1977).

Bhuyan, K.C. et al—*Mechanism of Cataractogenesis Induced by 3–amino–1H–1,2,4–triazole. I: Morphology and Histopathology of Cataract and the Role of Catalase in the Regulation of H2O2 in the Eye*, Biochemical and Clinical Aspects of Oxygen, 785–796 (1979).

Clark, A.F.—*Evaluation of Anti–Glaucoma Compounds And Discovery Of Pathogenic Mechanisms Using Perfusion Cultured Human Eyes*, Exp. Eye Res. 55:266 (1992).

Ellis, P.P.—*Basic Considerations* (Chap. 1), *Therapy of Diseases of the Cornea* (Chap. 11), *Therapy of Glaucomas* (Chap 13), Ocular Therapeutics and Pharmacology, pp. 3–27, 137–157, 162–186 (7th ed 1985).

(List continued on next page.)

*Primary Examiner*—Zohreh Fay
*Attorney, Agent, or Firm*—Howrey & Simon

[57] ABSTRACT

The invention concerns the recognition that certain non-steroidal anti-inflammatory agents can overcome or ameliorate limitations on trabecular meshwork cell division produced by environmental stresses (e.g., oxidative or phagocytic injury, or glucocorticoid exposure), and thus can be used to prevent or treat loss of trabecular cells found in certain forms of glaucoma and in normal aging. The use of such non-steroidal anti-inflammatory agents can ameliorate the severity, or prevent glaucoma.

29 Claims, No Drawings

OTHER PUBLICATIONS

Epstein, D.L.—*Chandler and Grant's Glaucoma*, pp. 3–5, 129–143, 181–183, 191, 194–195, 201–210, 211, 293–294, 311, 320–321, 352–379, 397 and 403–407 (3d ed. 1986).

Flach, A.J.—*Cyclo-oxygenase Inhibitors in Opthalmology*, Survey of Ophthalmology, 36:259–284 (1992).

Fauss, D.J. et al.—*Glucocorticoid (GC) Effects on HTM Cells: Biochemical Approaches and Growth Factor Responses*, Basic Aspects of Glaucoma Research III, pp. 319–330 (1993).

Giblin, F.J. et al.—*The Role of Glutathione Metabolism in the Detoxification of H2O2 in Rabbit Lens*, Invest. Ophthalmol. Vis. Sci. 22:330–335 (1982).

Huk, B. et al.—*Anti-Inflammatory Treatment after Argon Laser Trabeculoplasty*, Ophthalmologica 203: 24–29 (1991).

Insel, P.A. et al.—*Analgesic-Antipyretics and Antiinflammatory Agents; Drugs Employed in the Treatment of Rheumatoid Arthritis and Gout*, Goodman and Gilman's The Pharmacological Basis of Therapeutics, pp. 638–641 (8th ed. 1990).

Kahn, M.G. et al.—*Glutathione in Calf Trabecular Meshwork and its Relation to Aqueous Humor Outflow Facility*, Invest. Ophthalmol. Vis. Sci. 24:1283–1287 (1983).

Klemetti, A.—*The Dexamethason Provocative Test: A Predictive Tool for Glaucoma?*, Acta Ophthalmol. 68:29–33 (1990).

Langer, R.—*Controlled Release of Macromolecules*, Chem. Tech. 12:98–105 (1982).

Lee, V.H.L.—*Review: New Directions in the Optimization of Ocular Drug Delivery*, J. Ocular Pharmacol. 6:157–164 (1990).

Leske, M.C. et al.—*Estimating Incidence from Age-Specific Prevalence in Glaucoma*, Amer. J. Epidemiol. 113:606–613 (1981).

Lombardino, J.G.—*Nonsteroidal Anti-inflammatory Drugs. Chapter Two: Inflammation—Mechansims and Mediators*, pp. 75–109 (1985).

*McGraw–Hill Encyclopedia of Science and Technology: Eye (vertebrate)* 8:544–552 (6th ed. 1987).

*McGraw–Hill Encyclopedia of Science and Technology: Glaucoma* 8:131–132 (6th ed. 1987).

Mullins, J.D. et al.—*Ophthalmic Preparations*, Remington's Pharmaceutical Sciences, Chap. 86, pp. 1581–1595 (18th ed. 1990).

Nguyen, K.P. et al—*Hydrogen Peroxide Removal by the Calf Aqueous Outflow Pathway*, Invest. Ophthalmol. Vis. Sci. 29:976–981 (1988).

Nguyen, T.D. et al.—*Glucocorticoid (GC) Effects on HTM Cells: Molecular Biology Approaches*, Basic Aspects of Glaucoma Research III, pp. 330–343 (1993).

Polansky, J.R. et al.—*Cellular Mechanisms Influencing the Aqueous Humor Outflow Pathway*, Principles and Practice of Ophthalmology, Chap. 13, pp. 226–251 (1994).

Polansky, J.R. et al.—*Cellular Injury from Sustained vs. Acute Hydrogen Peroxide Exposure in Cultured Human Corneal Endothelium and Human Lens Epithelium*, CLAO Journal Supp. 16:S23–S29 (1990).

Polansky, J.R. et al.—*Human Trabecular Cells*, Invest. Ophthalmol. Vis. Sci. 18:1043–1049 (1979).

Polansky, J.R. et al.—*Studies on Human Trabecular Cells Propagated in Vitro*, Vision Res. 21:155–160 (1981).

Polansky, J.R. et al.—*In Vitro Correlates of Glucocorticoid Effects on Intraocular Presszure*, Glaucoma Update IV, pp. 20–29 (1991).

Polansky, J.R. et al.—*Eicosanoid Production and Glucocorticoid Regulatory Mechanisms in Cultured Human Trabecular meshwork Cells*, The Ocular Effects of Prostaglandins and other Eicosanoids, pp. 113–138 (1989).

Polansky, J.R.—*Side Effects of Topical Ophthalmic Therapy With Anti-Inflammatory Steroids and B-Blockers*, Current Opinion in Ophthalmology 3;259–272 (1992).

Polansky, J.R. et al.—*Growth Factor Effects and Modulation of Glucocorticoid (GC) and Other Stress Responses in Human Trabecular Meshwork (HTM) Cells*, Experimental Eye Research 55:265 1992).

Polansky, J.R.—*Basic Pharmacology of Corticosteroids*, Current Topics in Ocular Inflammation, No. 1, pp. 9–21 (1993).

Polansky, J.R. et al.—*HTM Cell Culture Model For Steroid Effects on Intraocular Pressure: Overview*, Basic Aspects of Glaucoma Research III, pp. 307–318 (1993).

Polansky, et al.—*Anti-inflammatory Agents: Steroids as Anti-Inflammatory Agents*, Handbook of Experimental Pharmacology 69:491–503 (1984).

Polansky, et al.—*Cellular Sensitivity to Glucocorticoids in Patients with POAG*, Investigative Ophthalmology & Visual Science 26:805–809 (1985).

Ringvold, A. et al.—*Electron Microscopy of the Trabecular Meshwork in Eyes with Exfoliation Syndrome*, Virchows Arch. Abt. A Path. Anat. 353:110–127 (1971).

Rohen, J.W. et al.—*The Phagocytic Activity of the Trabecular Meshwork Endothelium*, Albrecht v. Graefes Arch. Clin. Exper. Ophthalmol. 175:143–160 (1968).

Shabo, A.L. et al.—*Observations on the Fate of Blood in the Anterior Chamber*, Amer. J. Ophthalmol. 73:25–36 (1972).

Sidman, K.R. et al.—*Controlled Release of Macromolecules and Pharmaceuticals from Synthetic Polypeptides Based on Glutamic Acid*, Biopolymers 22:547–556 (1983).

Snyder, R.W. et al.—*Corticosteroid Treatment and Trabecular Meshwork Proteases in Cell and Organ Culture Supernatants* Exp. Eye Res. 57:461–468 (1993).

Spector, A. et al.—*Hydrogen Peroxide and Human Cataract*, Exp. Eye Res. 33:673–381 (1981)

Strong, N.P.—*How Optometrists Screen for Glaucoma: A Survey*, Ophthal. Physiol. Opt. 12:3–7 (1992).

Trier, K. et al.—*The Use of Estrogens in the Preparation of Formulation For Topical Treatment of High Pressure in the Eyes*, Chemical Abstracts 117:56002d (1992).

Vaughan, D. et al.—*Glaucoma*, General Ophthalmology, Chap. 11, pp. 213–230 (1992).

Weinreb, R.N. et al.—*Prostaglandin Production by Human Trabecular Cells: In Vitro Inhibition by Dexamethasone*, Invest. Ophthalmol. & Vis. Sci. 24:1541–1545 (1983).

Yun, A.J. et al.—*Proteins Secreted by Human Trabecular Cells*, Invest. Ophthalmol. Vis. Sci. 30:2012–2022 (1989).

Zhan, G. et al.—*Steroid Glaucoma: Corticosteroid-induced Ocular Hypertension in Cats*, Exp. Eye Res. 54:211–218 (1992).

Zun, L.S.—*Formulary of Commonly Used Ophthalmologic Medications*, Emerg. Med. Clin. North. Amer. 6:121–126 (1988).

Polansky, J.R., et al. *In Vitro Studies of Human Trabecular Cells: Perspectives and Limitations*, Proc. Int. Soc. for Eye Research, vol. I, p. 3 (1980).

Polansky, J.R., et al. *Glucocorticoid Receptors and Steroid Glaucoma Mechanisms*, Encounters in Glaucoma Research I: Receptor Biology and Gluacoma, pp. 273–299 (Feb. 1994).

Synder, R.W. et al. "Corticosteroid treatment and trabecular meshwork proteases in cell and organ culture supernatants", *Exp. Eye. Res.*, 57:4 461–468 (1993).

Database Pharma Projects, PJB Publications Ltd., Dialog File 928 Accession Nr. 021312, (1996).

Herbort et al. "Anti–inflammatory Effect of Topical Diclofenac After Argon Laser Trabeculoplasty", *Klin. Mbl. Augenheik*, 200:358–361 (1992).

InSite Vision Annual Report (1993).

Gerritsen et al., "Prostaglandin Synthesis and Release from Cultured Human Trabecular Meshwork Cells and Scleral Fibroblasts". *Exp. Eye. Res.* 43:1089–1102 (1986).

METHOD FOR THE TREATMENT OF A TRABECULAR MESHWORK WHOSE CELLS ARE SUBJECT TO INHIBITION OF CELL DIVISION

The present invention is in the field of therapeutics, and concerns methods and reagents for enhancing the mitotic rate of the cells of a trabecular meshwork whose cells are subject to an inhibition in cell division. This invention was supported with Government funds (NIH EY02477 and NIH EY 08905-02). The Government has certain rights in this invention.

FIELD OF THE INVENTION

BACKGROUND OF THE INVENTION

"Glaucomas" are a group of debilitating eye diseases that are the leading cause of blindness subject to positive intervention in the United States and other developed nations. The term "glaucoma" actually encompasses a variety of ophthalmic disease states which are caused by distinct disease processes or pathological conditions of the eye. The disease states under the term "glaucoma" generally share the characteristic of having elevated intraocular pressure ("IOP"), which is a major risk factor in producing visual field loss and blindness. Of the many different ophthalmic disease states, Chandler et al. (Glaucoma, 3d Ed., Lea and Febliger, Philadelphia (1986)) describe the following forms: primary open-angle glaucoma ("POAG"), progressive low-tension glaucoma, exfoliation and open-angle glaucoma ("OAG"), amylodosis and open-angle glaucoma, pigment dispersion and pigmentary glaucoma, angle-closure glaucoma, combined open-angle and angle-closure glaucoma, malignant glaucoma, angle-closure glaucoma after scleral buckling operations for separated retina, angle-closure glaucoma due to a multiple cyst of iris and ciliary body, angle-closure glaucoma secondary to occlusion of the central retinal vein, angle-closure glaucoma secondary to bilateral transitory myopia, glaucoma from perforating injuries, glaucoma from contusion of the eye, hemolytic or ghost-cell glaucoma, glaucoma associated with congenital and spontaneous dislocations of the lens, lens-induced glaucoma, glaucoma in aphasia, glaucoma due to intraocular inflammation, neovascular glaucoma, glaucoma associated with extra ocular venous congestion, essential atrophy of the iris with glaucoma, corticosteroid glaucoma, glaucoma after penetrating keratoplasty and characteristically unilateral glaucomas. In almost all cases, the IOP found in these glaucoma syndromes results from an increase in aqueous outflow resistance (see, Vaughan, D. et al., In: *General Ophthamology*, Appleton & Lange, Norwalk, Conn., pp. 213–230 (1992)).

Primary open-angle glaucoma ("POAG"), also termed chronic open-angle glaucoma ("COAG"), is the most prevalent form of glaucoma. The incidence of this condition in persons over the age of forty is about 0.4–0.5%. (Leske, M. C. et al., *Amer. J. Epidemiol.* 113:1843–1846 (1986); Bengtsson, B., *Br. J. Ophthamol.* 73:483–487 (1989); Strong, N. P., *Ophthal. Physiol. Opt.* 12:3–7 (1992)). Moreover, the prevalence of the disease rises with age to over 6% of those 75 years or older (Strong, N. P., *Ophthal. Physiol. Opt.* 12:3–7 (1992)). POAG is characterized by the loss of trabecular meshwork endothelial cells which is associated with degeneration of the normal structure of the trabecular meshwork. This degeneration leads to the obstruction of the normal ability of aqueous humor to leave the eye (see, Vaughan, D. et al., In: *General Ophthamology*, Appleton & Lange, Norwalk, Conn., pp. 213–230 (1992)).

In ordinary terminology, glaucoma is called "primary" if the pathogenic defect is believed to occur primarily within the tissue itself and without an obvious outside causal mechanism which can be defined for "secondary" glaucomas (e.g., see McGraw-Hill *Encyclopedia of Science and Technology*, 6th Ed., Vol. 8, p. 131 (McGraw-Hill 1987). In both POAG (for which no precise cause is known, although toxic substances produced locally and/or from the aqueous humor are believed to account for trabecular cell damage/death) and pigmentary glaucoma (often classified as a secondary glaucoma since the pigment or other debris from the posterior iris is thought to produce damage when engulfed by trabecular meshwork cells) there is known to be a marked loss of the endothelial cells of the meshwork. It is possible that oxidation products play a role in producing damage in the trabecular meshwork in both of these conditions, as well as in ocular iron toxicity, which can also produce a glaucoma. It would be very important to overcome the loss of trabecular meshwork endothelial cells which occurs in the disease processes. A loss in the number of trabecular meshwork cells and alteration in the function of the remaining cells is believed to be responsible for a decrease in the normal ability of aqueous humor to leave the eye, leading to decreased outflow facility (increased outflow resistance), and elevated IOP.

It previously has been demonstrated that aging itself leads to a progressive loss of human trabecular meshwork cells which also eventually leads to a compromise of the meshwork structure over time. Indeed, increased outflow resistance appears to occur in the non-glaucomatous aging population, and a method to encourage the cells in an aging normal individual to divide as well as those with a recognized chronic glaucoma syndrome would be highly desirable. A means to overcome the loss by encouraging cell division (or by other means) of trabecular cells is particularly important since this is believed to be a major factor in loss of trabecular meshwork structure that leads to elevated IOP and associated glaucomatous field loss. Even with optimal medical and surgical therapy the glaucomatous increase in IOP often becomes resistant to current therapies, leading to progressive visual loss and blindness.

Human trabecular meshwork cell division is an important homeostatic mechanism by which the cell number in the meshwork is maintained. A normal ability to divide is believed important to replace human trabecular meshwork cells lost to injury and aging. Meshwork cell division is observed to be decreased when tissues from older individuals and those with POAG are examined in tissue culture, most likely due to cumulative stress from a variety of factors (e.g., oxidative, phagocytic and or glucocorticoid stresses).

Elevated IOP results in progressive visual loss and blindness if not treated appropriately and in a timely fashion. The normal IOP for humans usually measures 10–20 mm Hg (1.3–2.7 kilopascals) and is maintained by a balance between the aqueous inflow and outflow; with rare exceptions, all glaucoma syndromes being associated with an outflow defect. The aqueous humor is produced by the ciliary body in the eye and passes from the posterior chamber through the papillary space into the anterior chamber. The aqueous drains through the trabecular meshwork into Schlemm's canal, through which it leaves the eye. Elevated IOP is considered a major risk factor in producing damage to the optic nerve head, leading to loss of visual fields and eventually to blindness in many patients. Even in so called "normal tension glaucoma," lowering of an apparently normal IOP is thought to help prevent visual loss.

A link between the IOP response of patients to glucocorticoids and the disease of POAG has long been suspected.

While only 5% of the normal population shows a high IOP increase (16 mm Hg) to topical glucocorticoid testing, over 90% of patients with POAG show this response. In addition, an open angle glaucoma may be induced by exposure to glucocorticoids. This observation has suggested that an increased or abnormal glucocorticoid response in trabecular cells may be involved in POAG (Zhan, G. L. et al., *Exper. Eye Res.* 54:211–218 (1992); Yun, A. J. et al., *Invest. Ophthamol. Vis. Sci.* 30:2012–2022 (1989); Clark, A. F., *Exper. Eye Res.* 55:265 (1992); Klemetti, A., *Acta Ophthamol.* 68:29–33 (1990); Knepper, P. A., U.S. Pat. No. 4,617,299)).

The ability of glucocorticoids to induce a glaucoma-like condition has led to efforts to identify genes or gene products that would be induced by the cells of the trabecular meshwork in response to glucocorticoids (Polansky, J. R. et al., In: *Glaucoma Update* IV, Springer-Verlag, Berlin, pp. 20–29 (1991)). In addition to the effect on specific gene products, another marked effect of glucocorticoid treatment to trabecular meshwork endothelial cells is the dramatic inhibition of cell division noticed when these cells were compared to a variety of other ocular and non-ocular cell types in culture (Fauss, D. J. et al., In: *Basic Aspects of Glaucoma Research III*, (Lutjen-Drecoll et al., eds.) Schattauer Press, New York, pp. 319–330 (1993)). A means to overcome the inhibition of cell division of trabecular meshwork cells produced by glucocorticoids as well as by oxidative injury would therefore also be useful.

In the currently available treatments for glaucoma, one attempts to symptomatically lower the IOP by decreasing the amount of inflow (decreasing the rate of aqueous formation) or by increasing the facility of outflow. Although outflow can be increased by a variety of drugs, as will be appreciated, the available treatments do not address the underlying pathogenic processes in POAG, pigmentary glaucoma and other syndromes associated with cell loss (nor do they address the trabecular meshwork cell loss associated with normal aging).

Examples of various drug treatments that symptomatically reduce IOP (see, e.g., Babcock, J. C. et al., U.S. Pat. No. 5,124,154; Epstein, D. L., U.S. Pat. No. 4,757,089; Doulakas, J., U.S. Pat. No. 4,829,088) include: pilocarpine and epheneprine, which owe their effectiveness to increasing the facility of outflow; as well as timolol and other beta blockers, carbonic-anhydrase-inhibiting drugs, and alpha adrenergic agents, which owe their effectiveness to decreasing the rate of formation of aqueous.

Doulakas (U.S. Pat. No. 4,829,088) discloses the use of an ophthalmic medicament containing diclofenac-sodium in aqueous solution for the treatment of inflammations of the eye. Diclofenac-sodium is a non-steroidal anti-inflammatory ("NSAI") agent which is believed to be an alternative to corticosteroids (glucocorticoids) for the treatment of some inflammatory symptoms in the eye, and appears especially useful for the symptomatic relief of pain. The aqueous solution is made suitable for the local treatment of inflammations of the eye due to its stability against chemical decomposition of the diclofenac-sodium and preservation properties and toleration by the eye.

Nagy (U.S. Pat. No. 4,960,799) discloses aqueous ophthalmic solutions containing diclofenac-sodium. The solutions, having a pH of about 7.8, comprise per milliliter of solution about 0.1 to about 5.0 milligrams of (a) pharmaceutically acceptable salt of ortho-(2,6-dichlophenyl-) aminophenyl acetic acid; (b) about 0.1 to about 10 milligrams of a pharmaceutically acceptable sale of ethylene diamine tetraccetic acid, (c) about 0.5 to about 200 milligrams of a pharmaceutically acceptable solubilizer, (d) about 0.01 to about 5.0 milligrams of a pharmaceutically acceptable bacteriostat and (e) the remainder water. The ophthalmic solutions are used for topical administration to the eye for the control or treatment of ocular inflammation.

Cherng-Chyi et al. (U.S. Pat. No. 5,110,493) relates to ophthalmic non-steroidal anti-inflammatory drug formulations containing a quaternary ammonium preservative and a non-ionic surfactant. The formulations are useful for treating diseases that are either caused by, associated with or accompanied by inflammatory processes.

The above, and others in the well-known class of NSAI agents have been proposed to suppress signs of inflammatory responses, to prevent particular side-effects of surgical trauma, especially fluid accumulating in the back of the eye, and the appearance of inflammatory cells and vessel leakage in the anterior chamber. NSAI agents useful in treating inflammation are known to inhibit prostaglandin production and also to affect other eicosanoid pathways. NSAI agents are believed to be a possible alternative for glucocorticoids to reduce inflammation and avoid side-effects due to these drugs (e.g., concealing the risk of deterioration as a result of bacterial or viral infection), but in practice, NSAI agents have proven to be much less effective in treating many different types of ocular inflammation.

There is no NSAI agent that has been proposed to encourage trabecular cell division or otherwise overcome the loss of trabecular cells associated with normal aging, nor in conditions in which cell loss and cell damage appear greater—as in POAG, pigmentary glaucoma and some other glaucoma syndromes.

The present invention provides improved therapeutic agents and methods by which certain cyclooxygenase inhibitors increase human trabecular meshwork cell division in these conditions.

SUMMARY OF THE INVENTION

The invention concerns the recognition that a loss of trabecular cells and loss of the normal structure of the trabecular meshwork contribute to the increased intraocular pressure that characterizes glaucomas.

The invention further concerns the recognition that certain non-steroidal anti-inflammatory agents (in addition to growth factors such a bFGF (basic fibroblast growth factor) help trabecular cells undergo cell division. Such agents can thus be used to treat the loss of trabecular cells observed in patients receiving glucocorticoids.

In detail, the invention provides a method for treatment of a trabecular meshwork whose cells are subject to inhibition of cell division, comprising administering to a human a composition including (a) an ophthalmologically effective amount of a non-steroidal cyclooxygenase inhibitor, and (b) a pharmaceutically acceptable carrier, to enhance the mitotic rate of the trabecular cells.

The invention also provides a method for treatment of a trabecular meshwork whose cells are subject to inhibition of cell division, comprising administering to a human a composition including (a) an ophthamologically effective amount of diclofenac, and (b) a pharmaceutically acceptable carrier, to enhance the mitotic rate of the trabecular cells, especially those cells whose mitotic rate has been compromised by pathogenic stress from a variety of sources.

The invention also provides a method for treatment of a trabecular meshwork whose cells are subject to inhibition of cell division from aging, glucocorticoid exposure or exposure to toxic substances, comprising administering to a human a composition including (a) an ophthalmically effective amount of a non-steroidal anti-inflammatory cyclooxygenase inhibitor and (b) a pharmaceutically acceptable inert carrier, to enhance the mitotic rate of the trabecular cells, especially those cells whose mitotic has been compromised by pathogenic stress from a variety of sources.

The invention particularly concerns the embodiment of the above methods wherein the NSAI agent is selected from the group of known cyclooxygenase inhibitor consisting of salicylates, indoles, phenylalkanoic acids, phenylacetic acids and pyrazolons, or from the group consisting of diclofenac, indomethacin and fenoprofen.

The invention additionally concerns the embodiment wherein the composition is administered topically (as in an aqueous polymeric solution, aqueous suspension, ointment or gel vehicle), or by intraocular injection, oral administration (as with an aqueous solution, aqueous suspension, elixir, tablet, caplet or capsule) and intravenous injection.

The invention also concerns the embodiment wherein the composition comprises (a) an ophthamologically effective amount of diclofenac, and (b) a pharmaceutically acceptable carrier, including a lightly cross-linked carboxy-containing polymer, in the form of an aqueous polymeric solution, suspension, ointment or gel for topical administration.

The invention also provides a composition adapted for enhancing the mitotic rate of trabecular meshwork cells subject to inhibition of cell division comprising (a) an ophthalmically effective amount of a non-steroidal anti-inflammatory cyclooxygenase inhibitor of a type and in an amount to enhance the mitotic rate of trabecular cells, and (b) a pharmaceutically acceptable inert carrier therefor.

DETAILED DESCRIPTION OF THE INVENTION

I. Overview of the Invention

Human trabecular meshwork (HTM) cells are endothelial-like cells that line the outflow channels by which aqueous humor exits the eye. As indicated above, the trabecular meshwork has been proposed to play an important role in the normal outflow of the aqueous fluid, and has been presumed to be the major site of outflow resistance in glaucomatous eyes.

An increased resistance to outflow through the trabecular meshwork is believed to cause the elevated IOP observed in POAG and other major glaucoma syndromes. The present invention pertains to a recognition that the health and viability of the cells which provide the endothelial lining of the trabecular meshwork structure are essential in preserving the integrity of the outflow channels. A loss in the number and/or function of these cells results in the development of pathological changes which lead to the collapse or covering of the structures of the outflow pathway, or otherwise compromise the normal function of such structure. The result of such changes is the increased outflow resistance observed in POAG and other forms of glaucoma (e.g., pigmentary glaucoma).

Glucocorticoids were introduced into ophthalmic practice over 40 years ago, soon after their ability to treat systematic inflammation and arthritis was recognized. Although such administration was beneficial in treating a variety of ocular inflammatory diseases, it was subsequently found to produce a high incidence of increased intraocular pressure (Polansky, J. R. et al., In: *Encounters in Glaucoma Research* 1: *Receptor Biology and Glaucom*," Anderson, D. E. et al., Eds., Fogliazza Editore, pp. 273–299 (1994); Polansky, J. R. et al., In: *Glaucoma Update IV*, Springer-Verlag, Berlin, pp. 20–29 (1991); Zhan, G. L. et al., *Exper. Eye Res.* 54:211–218 (1992)), and to cause glaucoma in some patients that after a long exposure may be irreversible (Polansky, J. R., *Curr. Opin. Ophthamol.* 3:259–272 (1992)).

Although many theories have been proposed to account for steroid-induced glaucoma, the mechanism of steroid-induced glaucoma has not been determined (Snyder, R. W. et al., *Exper. Eye Res.* 57:461–468 (1993); Polansky, J. R. et al., In: Principles and Practice of Ophthalmology, page 226–247, W. B. Saunders & Company, Philadelphia (1994)).

One aspect of the present invention concerns the recognition that the reduced outflow ability of the meshwork that is observed in glaucomatous and other patients is caused in part by conditions that diminish the capacity of the meshwork cells to undergo cell division. Relevant conditions are aging, exposure to glucocorticoids, and exposure to toxic substances (such as peroxides, pigment, debris, etc.) whose release is exacerbated by glucocorticoid exposure. A consequence of such inhibition is a decrease in the number of cells, and alteration of the function of the remaining cells, in the meshwork of eyes that have been exposed to such conditions. These alterations produce changes in the meshwork structure that, in turn, reduce the outflow facility and cause the elevated IOP of POAG, pigmentary glaucoma, some other glaucoma syndromes and normal aging.

A second aspect of the present invention concerns the recognition that non-steroidal anti-inflammatory ("NSAI") agents are able to counter the effect of such injury by increasing the mitotic rate of effected meshwork cells. Such agents therefore may be used to treat chronic glaucomas or pigmentary glaucoma that are induced or aggravated by the loss of trabecular meshwork cells. As used herein, the "mitotic rate" of meshwork cells is the rate at which new cells are formed via mitosis. The invention thus provides a method for treatment of a trabecular meshwork whose cells are "subject to inhibition of cell division". As used herein, cells are said to be "subject to inhibition of cell division" if the cells have been, are being, or will be exposed to an inhibitor of cell division (such as glucocorticoids, etc.) or a cellular process (such as aging) that effects cell division.

NSAI agents have been previously used in the eye primarily to treat inflammatory conditions and pain (see, for example, U.S. Pat. Nos. 4,960,799; 4,829,088, 5,110,493). This includes their application as topical agents in the eye, in which their ability to suppress inflammatory responses and to prevent particular side-effects of surgical trauma (on the pupil preventing surgical meiosis), fluid accumulating in the back of the eye after cataract surgery (post-surgical macular edema) and the appearance of inflammatory cells and vessel leakage in the anterior chamber. Topical application of NSAI agents in the eye also appear to relieve some of the itching due to allergic conjunctivitis. These conditions fit in the normal and expected effects of NSAI agents in inflammation and pain. In view of the known mechanisms of action of NSAI agents to lower prostaglandin (and other eicosanoid) production, it is quite surprising that such agents can affect trabecular cell division.

The concept that NSAI agents could be used in the treatment of "inflammatory glaucoma" (i.e., inflammation in the anterior part of the eye (anterior uveitis) has been previously proposed. In this glaucoma syndrome, it is thought that inflammatory cells from acute inflammation contribute to an elevated IOP which can become very dangerous if not treated. It was proposed, but never proven, that this glaucoma syndrome might be treated by decreasing inflammation with NSAI agents. Because NSAI agents have not been found to have a major effect in treating inflammatory glaucoma, they are not generally used for this condition. Instead, corticosteroids are the drugs of choice to treat inflammation in patients with inflammatory glaucoma; these drugs are used along with palliative measures that help to keep the IOP down, until inflammatory processes are brought under control.

II. The Preferred Agents of the Invention

The preferred agents of the present invention comprise non-steroidal anti-inflammatory agents that are able to prevent or lessen a damage to, or a loss of, trabecular cells, that is caused by a variety of mechanisms including oxidative injury to the tissues of the eye, and especially to the trabecular meshwork.

One class of NSAI agents that may be used in accordance with the methods of the present invention are "eicosanoid inhibiting agents." Eicosanoid inhibiting agents include those compounds which inhibit prostaglandin and other eicosanoid or cyclooxygenase pathways which are believed to affect IOP. Compounds considered within the classification of eicosanoid inhibitors include certain NSAI agents.

NSAI agents have been documented by J. Lombardino in *Nonsteroidal Anti-inflammatory Drugs*, Wiley-Interscience, New York, (1985). Examples of compounds of this class of anti-inflammatory drugs include but are not limited to the following: aspirin, benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketoprofen, lactorolac, lonazolac, metiazinic, miroprofen, naproxen, oxaprozin, oxepinac, phenacitin, pirprofen, pirazolac, protizinic acid, sulindac, suprofen, tiaprofenic acid, tolmetin, and zomepirac.

Non-steroidal eicosanoid inhibiting compounds can be prepared in the form of pharmaceutically acceptable salts, esters and other prodrugs. Derivative salts include relatively non-toxic inorganic or organic acid addition salts or alkaline earth metal salts of the therapeutic compounds, which can be prepared in situ during the final isolation and purification of the compounds or by separately reacting the free base with a suitable organic or inorganic acid. Where the compounds include a basic functionality such as amine or alkylamine, representative salts include hydrochloride, sulfate, acetate, maleate, lauryl sulphate, and the like. Where an acidic functionality is present, salts such as sodium, calcium, potassium and magnesium salts may be formed.

Additional examples of NSAI agents include non-narcotic analgesic/non-steroidal anti-inflammatory compounds such as (1) propionic acid derivatives, (2) acetic acid derivatives, (3) fenamic acid derivatives, (4) biphenylcarboxylic acid derivatives and (5) oxicams.

While some of these agents are primarily used at the present time as anti-inflammatory agents and others are primarily used as analgesics, in fact all of the contemplated compounds have both analgesic and anti-inflammatory activity and can be used at appropriate dosage levels for either purpose in various compositions.

The compounds in groups (1) through (4) typically contain a carboxylic acid function; however, those acids are sometimes administered in the form of their pharmaceutically acceptable acid addition or alkali metal salts, e.g., sodium salts.

The propionic acid derivatives include, but are not limited to, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alimoprofen, tiaprofenic acid, fluprofen and bucloxic acid. Structurally related propionic acid derivatives having similar analgesic and anti-inflammatory properties are also intended to be encompassed by this group.

Thus, "propionic acid derivatives" as defined herein are non-narcotic analgesics/non-steroidal anti-inflammatory drugs having a free —CH(CH₃)COOH or —CH2CH₂COOH group (which optionally can be in the form of a pharmaceutically acceptable salt group, e.g., —CH(CH₃)COO⁻Na⁺), typically attached directly or via a carbonyl function to a ring system, preferably to an aromatic ring system.

Acetic acid derivatives as defined herein include, but are not limited to, indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g., —CH₂COO⁻Na⁺), typically attached directly to a ring system, preferably to an aromatic or heteroaromatic ring system.

Fenamic acid derivatives as defined herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. Thus, "fenamic acid derivative" as defined herein are non-narcotic analgesics/non-steroidal anti-inflammatory drugs which contain the basic structure

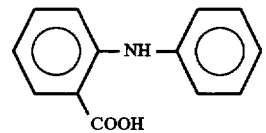

which can bear a variety of substituents and in which the free —COOH group can be in the form of a pharmaceutically acceptable salt group, e.g., —COO⁻NA⁺.

The biphenylcarboxylic acid derivatives as defined herein include, but are not limited to, diflunisal and flufenisal. Structurally related biphenylcarboxylic acid derivatives having similar analgesic and anti-inflammatory properties are also intended to be encompassed by this group.

Thus, "biphenylcarboxylic acid derivative" as defined herein are non-narcotic analgesics/non-steroidal anti-inflammatory drugs which contain the basic structure

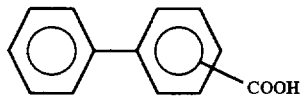

which can bear a variety of substituents and in which the free —COOH group can be in the form of a pharmaceutically acceptable salt group, e.g., —COO⁻NA⁺.

The oxicams as defined herein include, but are not limited to, piroxicam, sudoxicam, isoxicam, and CP-14,304. Structurally related oxicams having similar analgesic and antiinflammatory properties are also intended to be encompassed by this group. A preferred member of this group is piroxicam.

Thus, "oxicams" as defined herein are non-narcotic analgesics/non-steroidal anti-inflammatory drugs which have the general formula:

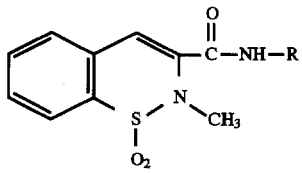

wherein R is an aryl or heteroaryl ring system.

Also included within the non-steroidal eicosanoid inhibitors or NSAI agents of the present invention are certain cyclooxygenase inhibitors as described by Flach, A. J., *Survey Ophthalmology* 36:259–284 (1992). Cyclooxygenase inhibitors are non-steroidal antiinflammatory drugs that have become available as ophthalmic eyedrops for treatment of inflammation. These inhibitors may be grouped into six different classes: salicylates, fenamates, indoles, phenylalkanoic acids and pyrazolones. Specific drugs within the respective groups are summarized below.

| Cyclo-oxygenase Inhibitors | |
|---|---|
| Chemical Class | Generic Name |
| Salicylates | Aspirin, Salicylic Acid, Diflunisol |
| Indoles | Indomethacin, Sulinda, Tolmetin |
| Phenylalkanoic acids | Fenoprofen, Flurbiprofen, Ibuprofen, Ketoprofen, Ketorolac, Naproxen, Piroxicam, Suprofen |
| Phenylacetic acids | Diclofenac |
| Pyrazolons | Oxyphenbutazone, Phenylbutazone, Antipyrine, Aminopyrine, Azapropazone |

III. Methods of Administration

The agents of the present invention can be formulated according to known methods to prepare pharmaceutically acceptable compositions, whereby these materials, or their functional derivatives, having the desired degree of purity are combined in admixture with a physiologically acceptable carrier, excipient, or stabilizer. Such materials are non-toxic to recipients at the dosages and concentrations employed.

A composition is said to be "pharmaceutically acceptable" if its administration can be tolerated by a recipient patient. An agent is physiologically significant if its presence results in a detectable change in the physiology of a recipient patient. Preferably, such compositions are administered topically in an aqueous polymeric solution, aqueous suspension, ointment or gel vehicle.

Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)).

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween, Pluronics, or PEG, e.g., Tween 80, in an amount of, for example, 0.04–0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinyl pyrrolidone; amino acids, such as glycine, glutamic acid, aspirin, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved through the use of polymers to complex or absorb the molecule(s) of the composition. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate) and the concentration of macromolecules as well as the methods of incorporation in order to control release.

Sustained release formulations may also be prepared, and include the formation of microcapsular particles and implantable 5 articles. For preparing sustained-release compositions, the molecule(s) of the composition is preferably incorporated into a biodegradable matrix or microcapsule. A suitable material for this purpose is a polylactide, although other polymers of poly-(α-hydroxycarboxylic acids), such as poly-D-(−)-3-hydroxybutyric acid (EP 133, 988A), can be used. Other biodegradable polymers include poly(lactones), poly(orthoesters), polyamino acids, hydrogels, or poly(orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Patent No. 1176565, Sidman, U. et al., *Biopolymers* 22:547 (1983), and Langer, R. et al., *Chem. Tech.* 12:98 (1982).

Alternatively, instead of incorporating the molecule(s) of the composition into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In an alternative embodiment, liposome formulations and methods that permit intracellular uptake of the molecule will be employed. Suitable methods are known in the art, see, for example, Chicz, R. M. et al. (PCT Application WO 94/04557), Jaysena, S. D. et al. (PCT Application WO93/12234), Yarosh, D. B. (U.S. Pat. No. 5,190,762), Callahan, M. V. et al. (U.S. Pat. No. 5,270,052) and Gonzalezro, R. J. (PCT Application 91/05771), all herein incorporated by reference.

The pharmaceutical compositions of the present invention may be sterilized, as by filtration through sterile filtration membranes (e.g., 0.2 micron membranes). The compositions may be stored in lyophilized form or as a liquid solution. It will be understood that use of certain of the foregoing excipients, carriers, or stabilizers will result in the formation of salts of the molecules.

The compositions of the present invention can be applied topically as to the skin, or to the cornea. When applied topically, the molecule(s) of the composition may be suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, and bandages, preferably in liquid or semi-liquid form.

For obtaining a gel formulation, the molecule(s) of the composition formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, non-toxic, simple to prepare, and not too runny or viscous, and will not destabilize the molecule(s) held within it. Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The compositions of the present invention can also be formulated for administration parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers, adjuncts or occlusive dressings can be used to increase tissue permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents. Alternative oral formulations include an aqueous solution, aqueous suspension, elixir, tablet, caplet or capsule.

If methylcellulose is employed in the gel, preferably it comprises about 2–5%, more preferably about 3%, of the gel and the molecule(s) of the composition is present in an amount of about 300–1000 µg per ml of gel. The dosage to be employed is dependent upon the factors described above. As a general proposition, the molecule(s) of the composition is formulated and delivered to the target site or tissue at a dosage capable of establishing in the tissue a maximum dose that is efficacious but not unduly toxic.

In the most preferred embodiment, the molecules of the invention will be provided to the cornea or surface of the eye, and permitted to absorb across the cornea into the anterior chamber of the eye. Methods that may be used for accomplishing such ocular drug delivery are described by Zun, L. S. (*Emerg. Med. Clin. North. Amer.* 6:121 (1988)), Lee, V. H. (*J. Ocular Pharmacol.* 6:157 (1990)), Ellis, P. P. (In: *Ocular Therapeutics and Pharmacology*, 7th ed., Mosby, (1987)), Jannsen, H. J. (U.S. Pat. No. 5,200,453), Chandrasekaran, S. K. et al. (PCT Appln. No. WO89/06964) and (Vaughan, D. et al., In: *General Ophthamology*, Appleton & Lange, Norwalk, Conn., pp. 213–230 (1992)).

Most preferably, however, such drug administration will be accomplished by combining effective amounts of the agents of the invention with any of the sustained release ophthalmic delivery systems described by Davis, J. P. et al. (U.S. Pat. No. 5,192,535, herein incorporated by reference).

Such preferred sustained release topical ophthalmic medicament delivery systems comprise an aqueous suspension at a pH of from about 3 to about 6.5 and an osmotic pressure of from about 10 to about 400 mOsM containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a crosslinking agent, such weight percentages of monomers being based on the total weight of monomers polymerized. Desirably the polymer is prepared by suspension or emulsion polymerizing the monomer with the crosslinking agent to a particle size of not more than about 50 µm, preferably not more than about 30 µm, in equivalent spherical diameter. The suspension has an initial viscosity of from about 1,000 to about 30,000 centipoises (cp) and is administrable to the eye in drop form at that initial viscosity. The polymer has average particle size of not more than about 50 µm, preferably not more than about 30 µm, in equivalent spherical diameter. In general, such polymers will range in molecular weight estimated to be about 250,000 to about 4,000,000, and preferably about 500,000 to about 2,000,000.

Aqueous suspensions containing polymer particles prepared by suspension or emulsion polymerization whose average dry particle size is appreciably larger than about 50 µm in equivalent spherical diameter are less comfortable when administered to the eye than suspensions otherwise identical in composition containing polymer particles whose equivalent spherical diameters are, on the average, below about 50 μm. Moreover, above the average 50 μm size, the advantage of substantially increased viscosity after administration is not realized.

The lightly crosslinked suspension is administrable in drop form, upon contact of the lower pH suspension with the higher pH tear fluid of the eye, the suspension is rapidly gellable to a substantially greater viscosity than the viscosity of the suspension as originally administered in drop form. Accordingly, the resulting more viscous gel can remain in the eye for a prolonged period of time so as to release its NSAI agent over a prolonged time period.

A preferred drug delivery system employs a polymer that is preferably prepared from at least about 50% by weight, more preferably at least about 90% by weight, of one or more carboxyl-containing monoethylenically unsaturated monomers. Acrylic acid is the preferred carboxyl-containing, monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), p-hydroxycoumaric acid (umbellic acid), and the like can be used in addition to or instead of acrylic acid. Carbopol 976 and polycarbophil (Davis, et al., U.S. Pat. No. 5,192,535) are examples of suitable polymers.

Such polymers are crosslinked by using a small percentage, i.e., less than about 5%, such as from about 0.5% or from about 0.1% to about 5%, and preferably from about 0.2% to about 1%, based on the total weight of monomers present, of a polyfunctional crosslinking agent. The crosslinking agents of such compositions include non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. A preferred crosslinking agent is divinyl glycol. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown, U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products, and reaction products of isocyanate terminated prepolymers derived from polyester diols, polyether diols or polysiloxane diols with hydroxyalkylmethacrylates, and the like, can also be used as the crosslinking agents; see, e.g., Mueller et al, U.S. Pat. Nos. 4,192,827 and 4,136,250.

In a preferred method of preparing sustained release topical ophthalmic delivery systems, the foregoing suspensions are prepared and packaged at the desired viscosity of from 1,000 to about 30,000 centipoises, for administration to the eye in drop form. In a preferred delivery method, the foregoing suspensions, containing the medicament, are administered to the eye at the initial viscosity in drop form to cause the administered suspension, upon contact with the higher pH tear fluid of the eye, to rapidly gel in situ to a substantially greater viscosity than the viscosity of the suspension as originally administered in drop form. The more viscous gel remains in the eye for a prolonged period of time so as to release the medicament, entrapped in the more viscous gel formed in the eye, in sustained fashion.

It may be desirable to replace up to about 40% by weight of the carboxyl-containing monoethylenically unsaturated monomers by one or more non-carboxyl-containing monoethylenically unsaturated monomers containing only physiologically and ophthamologically innocuous substituents.

The desired osmotic pressure is preferably achieved by using a physiologically and ophthalmologically acceptable salt in an amount of from about 0.01% to about 1% by weight, based on the total weight of the suspensions. A preferred salt is sodium chloride.

Generally, the dosage needed to provide an effective amount of the composition will vary depending upon such factors as the recipient's age, condition, sex, and extent of disease, if any, and other variables, and can be adjusted and determined by one of ordinary skill in the art. Effective amounts of the compositions of the invention can vary from 0.01–1,000 mg/ml per dose or application, although lesser or greater amounts can be used. For ophthalmic suspensions, the effective amounts will preferably be from about 0.0001% to about 10% by weight, and most preferably from about 0.01% to about 5% by weight, based on the total weight of the suspension.

For example, to enhance the mitotic rate of cells of a trabecular meshwork whose cells are subject to an inhibition of cell division, the composition of an ophthalmologically effective amount of a non-steroidal cyclooxygenase inhibitor, and a pharmaceutically acceptable carrier contains between about 0.001% and about 10% by weight amount of the non-steroidal cyclooxygenase inhibitor. The same compositions can be used to provide treatment of a trabecular meshwork whose cells are subject to inhibition of cell division from aging, glucocorticoid exposure or exposure to toxic substances. Most preferably, for either use, the composition is administered to provide a concentration of inhibitor of less than about $1 \times 10^{-5}$M (and preferably between about $1 \times 10^{-9}$M and about $1 \times 10^{-5}$M) in the aqueous humor of the eye.

Having now generally described the invention, the same will be more readily understood through reference to the following examples which are provided by way of illustration, and are not intended to be limiting of the present invention, unless specified.

EXAMPLE 1

Effect of Peroxide on Growth of Cultured Trabecular Meshwork Cells Subjected to Oxidative Stress The effect of hydrogen peroxide exposure on the capacity of cultured trabecular meshwork cells to continue proliferating was investigated.

Human trabecular cells were exposed to oxidative injury by rinsing once with 37° C. Phosphate Buffered Saline solution (PBS) and then adding PBS or 0.3 mM hydrogen peroxide ($H_2O_2$) diluted with PBS. The cells were then placed in a 37° C. water jacketed incubator. After 30 minutes, the cells were rinsed twice with PBS-CMF (calcium-free, magnesium-free PBS). STV (0.05% trypsin, 0.02% versene (EDTA) in Saline A (8 g/l NaCl, 0.4 g/l KCl, 0.005 g/l phenol red)) was added and the cells were then incubated at room temperature until they became detached from the culture dish. The cells were then placed in their normal culture media (10% fetal calf serum (FCS)-

Dulbecco's Modified Eagle's Media (DME) (or 10% FCS DME)). An aliquot of this solution was counted on a Coulter Counter (Model ZF) and the cells were then diluted with culture media and plated onto culture dishes at 1200 cells/cm$^2$. The cells were then placed in a 37° C. water-jacketed 8% $CO_2$ incubator. The following day, the culture media was changed and the cells were treated either with or without Vitamin E acetate, acetaminophen or ibuprofen. The culture media was again changed and the cells likewise treated three days after the initial plating. Four days after the initial plating, the cells were rinsed twice with PBS-CMF. STV was then added and the cells were incubated at 37° C. for 10 minutes. The cells were then counted on a Coulter Counter (Model ZF). As shown in Table 1, $H_2O_2$ inhibited the ability of the cells to divide. This effect was slightly reversed by subsequent treatment with Vitamin E acetate. Ibuprofen treatment at 10 µM brought the level of cell division up to the level of the untreated cells whereas acetaminophen had no effect. Table 1 shows the cells/cm$^2$ of peroxide treated samples relative to the control.

TABLE 1

| Treatment | Concentration Of Drug | Relative Cells/cm$^2$ | |
|---|---|---|---|
| | | 0 mM $H_2O_2$ | 0.3 mM $H_2O_2$ |
| Control | 0 | 100 | 11 |
| Vitamin E Acetate | 10 µM | | 20 |
| Acetaminophen | 10 µM | | 6 |
| Ibuprofen | 1 µM | | 71 |
| Ibuprofen | 10 µM | | 100 |

EXAMPLE 2

Effect of NSAI Agents on the Cell Division of Cultured Human Trabecular Meshwork Cells Treated with and without Dexamethasone The effect of NSAI agents on the cell division of cultured human trabecular cells treated with and without dexamethasone was investigated.

Human trabecular cells were grown to confluency as previously described (Polansky, J. R. et al., *Invest. Ophthamol. Vis. Sci.* 18:1043 (1979); Alvarado, J. A. et al., *Invest. Ophthamol. Vis. Sci.* 23:464 (1982); Polansky, J. R. et al., Proc. Int. Soc. Eye Res. 3:76 (1980); Nguyen, T. D. et al., In: "*Schriftenreihe de Adademie der Wissenschaften und der Literatur, Mainz,*" 331–343 (1993); Polansky, J. R. et al., *Vision Res.* 21:155 (1981); Polansky, J. R. et al., In: Principles and Practice of Ophthalmology, page 226–247, W. B. Saunders & Company, Philadelphia (1994), all herein incorporated by reference). The cells were rinsed twice with calcium-free, magnesium-free, phosphate buffered saline solution (PBS-CMF). STV (0.05% trypsin, 0.02% versene (EDTA) in Saline A (8 g/l NaCl, 0.4 g/l KCl, 0.005 g/l phenol red)) was added and the cells were then incubated at room temperature until they became detached from the culture dish. The cells were then placed in the normal culture media (10% fetal calf serum (FCS)-Dulbecco's Modified Eagles Media (DME) (or 10% FCS DME)). An aliquot of this solution was counted on a Coulter Counter (Model ZF) and the cells were then diluted with culture media and plated onto culture dishes at 2500 cells/cm$^2$. The cells were then placed in a 37° C. water-jacketed 8% $CO_2$ incubator. The following day, the culture media was changed and the cells were treated with diclofenac (0.01, 0.1, 1 µM), flurbiprofen (0.01, 0.1, 1 µM), aspirin (1, 10 µM), or acetaminophen (1, 10 µM), either with or without 500 nM dexamethasone.

The culture media was again changed and the cells likewise treated three and five days after the initial plating. Seven days after the initial plating, the cells were rinsed twice with PBS-CMF. STV was then added and the cells were incubated at 37° C. for 10 minutes. The cells were then counted on a Coulter Counter (Model ZF). Table 2 shows the effect of NSAI Agents on the rate of human trabecular meshwork cell division in the presence of 500 nM dexamethasone. As shown in Table 2, diclofenac, flurbiprofen and aspirin each affected the rate of cell division to different degrees while no effect was found for acetaminophen. Table 2 also shows that while dexamethasone inhibited the rate of cell division, this effect was overcome by co-treatment with diclofenac, flurbiprofen and aspirin but not by co-treatment with acetaminophen. In Table 2, the "Relative Cell Number" denotes the cell number obtained relative to the control with 0 nM dexamethasone. As will be appreciated, the concentrations employed in Table 2 are illustrative of the present invention, but do not define concentration limits; greater or lesser concentrations of NSAI agents may be employed to obtain increased or more gradual enhancement of human trabecular 10 meshwork mitotic rate.

TABLE 2

| Treatment | Concentration of Drug (µM) | Relative Cell Number Dexamethsone | |
|---|---|---|---|
| | | 0 nM | 500 nM |
| Control | 0 | 100 | 41 |
| Diclofenac | 0.01 | | 72 |
| Diclofenac | 0.1 | | 106 |
| Diclofenac | 1 | | 144 |
| Flurbiprofen | 0.01 | | 50 |
| Flurbiprofen | 0.1 | | 52 |
| Flurbiprofen | 1 | | 88 |
| Aspirin | 1 | | 45 |
| Aspirin | 10 | | 68 |
| Acetaminophen | 1 | | 34 |
| Acetaminophen | 10 | | 44 |

The data in Table 3 demonstrates the ability of NSAI agents to increase human trabecular meshwork cell division in cells that have not been exposed to glucocorticoids. As such, the methods of the present invention may be used to repopulate human trabecular meshwork cells that have been lost via processes such as aging.

TABLE 3

| Treatment | Concentration of Drug (µM) | Relative Cell Number |
|---|---|---|
| Control | 0 | 100 |
| Diclofenac | 1 | 212 |
| Flurbiprofen | 1 | 233 |
| Aspirin | 1 | 101 |
| Acetaminophen | 1 | 95 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for treatment of a trabecular meshwork whose cells are subject to inhibition of cell division, comprising administering to a human a composition including (a) an ophthalmologically effective amount of a non-steroidal cyclooxygenase inhibitor, and (b) a pharmaceutically acceptable carrier, to enhance the mitotic rate of said trabecular cells.

2. The method according to claim 1, wherein said cyclooxygenase inhibitor is selected from the group consisting of salicylates, indoles, phenylalkanoic acids, phenylacetic acids and pyrazolons.

3. The method according to claim 1, wherein said non-steroidal cyclooxygenase inhibitor is selected from the group consisting of diclofenac, indomethacin and fenoprofen.

4. The method according to claim 1, wherein said composition is administered topically in an aqueous polymeric solution, aqueous suspension, ointment or gel vehicle.

5. The method according to claim 1, wherein said composition comprises between about 0.001 and about 10% by weight of said cyclooxygenase inhibitor.

6. The method according to claim 5, wherein said composition comprises between about 0.001 and about 0.009% by weight of said inhibitor.

7. The method according to claim 1, wherein said composition is administered to provide a concentration of said inhibitor of less than about $1\times10^{-5}$M in the aqueous humor of the eye.

8. The method according to claim 7, wherein said composition is administered to provide a concentration of said inhibitor of between about $1\times10^{-9}$M and about $1\times10^{-5}$M in the aqueous humor of the eye.

9. The method according to claim 1, wherein said composition is administered by a method selected from the group consisting of intraocular injection, oral administration and intravenous injection.

10. The method according to claim 9, wherein said composition is administered orally, and wherein the composition is an aqueous solution, aqueous suspension, elixir, tablet, caplet or capsule.

11. A method for treatment of a trabecular meshwork whose cells are subject to inhibition of cell division, comprising administering to a human a composition including (a) an ophthamologically effective amount of diclofenac, and (b) a pharmaceutically acceptable carrier, to enhance the mitotic rate of said trabecular cells.

12. The method according to claim 11, wherein said pharmaceutically acceptable carrier is a topical formulation of an aqueous polymeric solution, suspension, ointment or gel.

13. The method according to claim 12, wherein said pharmaceutically acceptable carrier includes a lightly cross-linked carboxy-containing polymer.

14. The method according to claim 13, wherein said diclofenac is present in said formulation in an amount from about 0.001% to about 10% by weight of the composition.

15. The method according to claim 14, wherein said diclofenac is present in said formulation in an amount from about 0.001% to about 0.009% by weight of the composition.

16. The method according to claim 15, wherein said composition is administered in an amount sufficient to provide an opthalmically effective amount of said diclofenac not exceeding $1\times10^{-5}$M in the aqueous humor of the eye.

17. A method for treatment of a trabecular meshwork whose cells are subject to inhibition of cell division from aging, glucocorticoid exposure or exposure to toxic substances, comprising administering to a human a composition including (a) an ophthalmically effective amount of a non-steroidal anti-inflammatory cyclooxygenase inhibitor and (b) a pharmaceutically acceptable inert carrier, to enhance the mitotic rate of said trabecular cells.

18. The method according to claim 17, wherein said non-steroidal anti-inflammatory cyclooxygenase inhibitor is selected from the group consisting of salicylates, indoles, phenylalkanoic acids, phenylacetic acids and pyrazolons.

19. The method according to claim 17, wherein said non-steroidal anti-inflammatory cyclooxygenase inhibitor is selected from the group consisting of diclofenac, indomethacin and fenoprofen.

20. The method according to claim 17, wherein said non-steroidal anti-inflammatory cyclooxygenase inhibitor is diclofenac.

21. The method according to claim 17, wherein said composition is administered topically in an aqueous polymeric solution, aqueous suspension, ointment or gel vehicle.

22. The method according to claim 17, wherein said composition comprises between about 0.001% and about 10% by weight of said eicosanoid inhibitor.

23. The method according to claim 22, wherein said composition comprises between about 0.001% and about 0.009% by weight of said inhibitor.

24. The method according to claim 23, wherein said composition is administered to provide a concentration of said inhibitor of less than about $1\times10^{-5}$M in the aqueous humor of the eye.

25. The method according to claim 24, wherein said composition is administered to provide a concentration of said inhibitor of between about $1\times10^{-9}$M and about $1\times10^{-5}$M in the aqueous humor of the eye.

26. The method according to claim 25, wherein said composition is administered by a method selected from the group consisting of intraocular injection, oral administration and intravenous injection.

27. The method according to claim 26, wherein said composition is administered orally, and wherein the composition is an aqueous solution, aqueous suspension, elixir, tablet, caplet or capsule.

28. The method of claim 17, wherein said inhibition of cell division is caused by aging.

29. The method of claim 17, wherein said inhibition of cell division is caused by glucocorticoid exposure or exposure to a toxic substance.

* * * * *